(12) United States Patent
Wang et al.

(10) Patent No.: US 7,887,682 B2
(45) Date of Patent: Feb. 15, 2011

(54) ANALYTE SENSORS AND METHODS OF USE

(75) Inventors: Yi Wang, San Ramon, CA (US); Benjamin J. Feldman, Oakland, CA (US); Jared L. Watkin, Danville, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1191 days.

(21) Appl. No.: 11/277,931

(22) Filed: Mar. 29, 2006

(65) Prior Publication Data

US 2007/0227911 A1  Oct. 4, 2007

(51) Int. Cl.
*G01N 27/26* (2006.01)
*G01N 27/30* (2006.01)

(52) U.S. Cl. ............ 204/403.01; 204/412; 204/409; 204/403.14; 204/411

(58) Field of Classification Search ............ 204/403.1, 204/403.01, 403.14, 403.12, 409, 411, 412; 205/792, 775, 779, 777.5; 422/82.01
See application file for complete search history.

(56) References Cited

U.S. PATENT DOCUMENTS

| | | | |
|---|---|---|---|
| 5,141,868 A | 8/1992 | Shanks et al. | |
| 5,989,409 A * | 11/1999 | Kurnik et al. | 205/792 |
| 6,071,391 A | 6/2000 | Gotoh et al. | |
| 6,156,173 A * | 12/2000 | Gotoh et al. | 204/403.04 |
| 6,299,757 B1 | 10/2001 | Feldman et al. | |
| 6,338,790 B1 | 1/2002 | Feldman et al. | |
| 6,447,657 B1 * | 9/2002 | Bhullar et al. | 204/403.01 |
| 6,461,496 B1 | 10/2002 | Feldman et al. | |
| 6,572,745 B2 | 6/2003 | Rappin et al. | |
| 6,592,745 B1 | 7/2003 | Feldman et al. | |
| 6,618,934 B1 | 9/2003 | Feldman et al. | |
| 6,749,740 B2 * | 6/2004 | Liamos et al. | 205/792 |
| 6,801,041 B2 | 10/2004 | Karinka et al. | |
| 7,208,077 B1 * | 4/2007 | Albers et al. | 205/782 |
| 7,563,350 B2 * | 7/2009 | Feldman et al. | 204/403.04 |
| 2003/0203498 A1 | 10/2003 | Neel et al. | |
| 2004/0200720 A1 * | 10/2004 | Musho et al. | 204/403.01 |
| 2004/0225230 A1 | 11/2004 | Liamos et al. | |
| 2004/0256248 A1 | 12/2004 | Burke et al. | |
| 2005/0016845 A1 | 1/2005 | Groll et al. | |
| 2005/0019953 A1 | 1/2005 | Groll | |
| 2005/0023137 A1 * | 2/2005 | Bhullar et al. | 204/403.1 |
| 2006/0144704 A1 | 7/2006 | Ghesquiere et al. | |

FOREIGN PATENT DOCUMENTS

| | | |
|---|---|---|
| EP | 1 211 321 A1 | 6/2002 |
| WO | WO 97/00441 | 1/1997 |
| WO | WO 98/43074 | 10/1998 |
| WO | WO00/62048 * | 10/2000 |
| WO | WO 2004/113914 A1 | 12/2004 |
| WO | WO 2004/113915 A1 | 12/2004 |
| WO | WO 2005/001474 A1 | 1/2005 |

* cited by examiner

*Primary Examiner*—Alexa D Neckel
*Assistant Examiner*—Jennifer Dieterle
(74) *Attorney, Agent, or Firm*—Edward J. Baba; Shweta Chandra; Bozicevic, Field & Francis LLP

(57) ABSTRACT

In vitro analyte sensors and methods of analyte determination are provided. Embodiments include sensors that include a pair of electrodes to monitor filling of the sample chamber with sample.

18 Claims, 13 Drawing Sheets

FIG. 3B
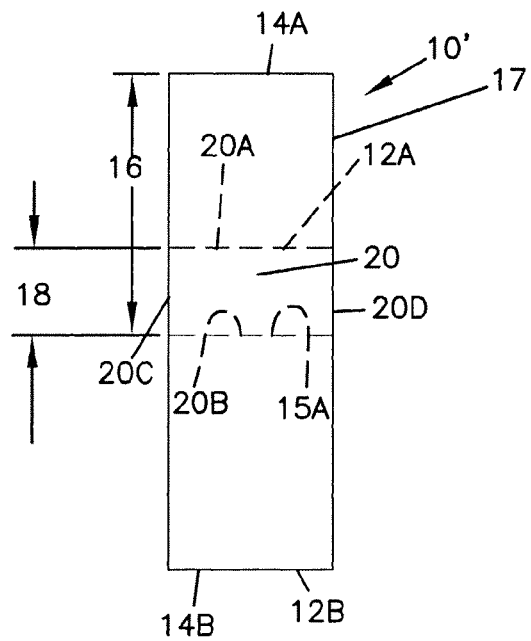
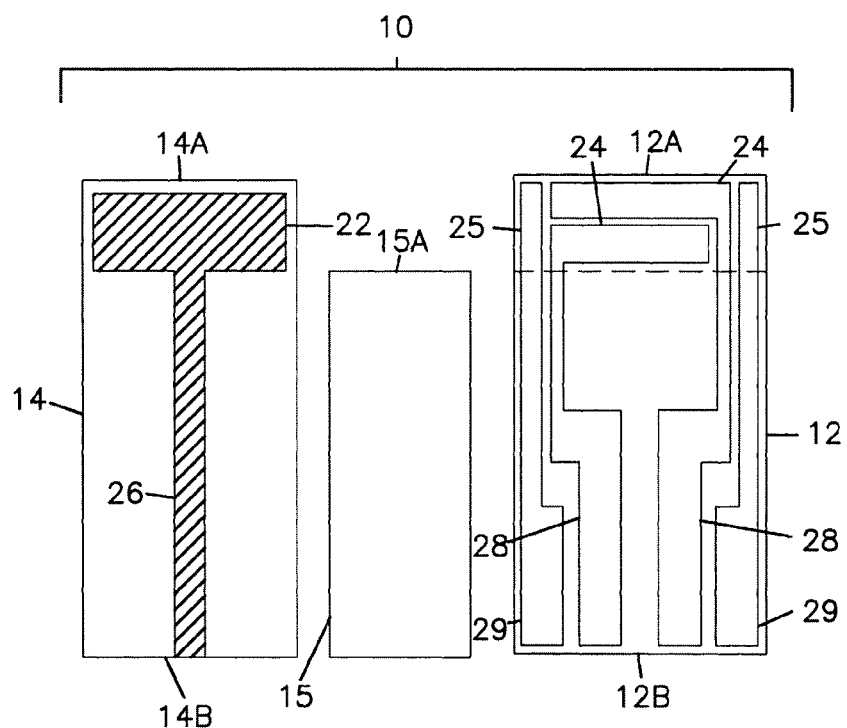
FIG. 4

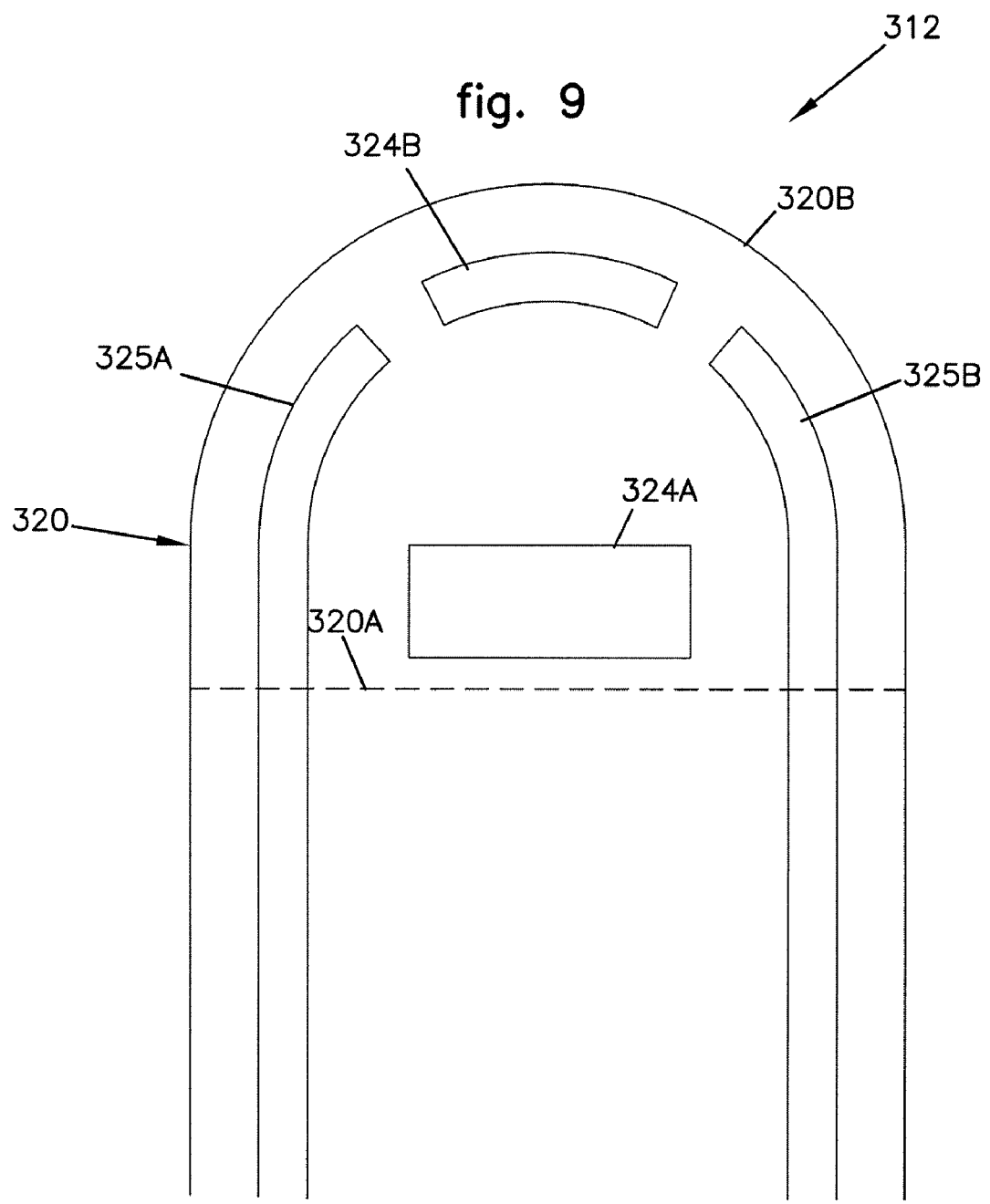

ANALYTE SENSORS AND METHODS OF USE

BACKGROUND OF THE INVENTION

Biosensors, also referred to as analytical sensors or merely sensors, are commonly used to determine the presence and concentration of a biological analyte in a sample. Such biosensors are used, for example, to monitor blood glucose levels in diabetic patients.

As sensors continue to be used, there continues to be an interest in sensors that are easy to manufacture and easy for a patient to use.

SUMMARY OF THE INVENTION

Embodiments of the present invention provide sensors, which have multi-directional fill capabilities, with a configuration that monitors the filling of the sample chamber, regardless of the direction from which the chamber is filled. More particularly, embodiments of the sensors of the present invention have an electrode configuration that monitors the filling of a multi-directional fill sample chamber, particularly a small volume sample chamber.

In some embodiments, the sensor includes two arrangements of electrodes, such as two pairs of electrodes, in the sample chamber, to monitor sample presence in the sample chamber in two directions or dimensions. For example, a first electrode arrangement detects presence of the sample crossing one of the dimensions of the sample chamber, and a second electrode arrangement detects whether or not the electrodes are sufficiently covered with sample to provide an acceptable result. In some embodiments, the first arrangement detects the sample presence in a first direction or dimension, and the second arrangement detects the sample presence in a second direction or dimension, which may be orthogonal to the first direction or dimension.

The sample chamber may be any suitable size, including large and small volume sample chambers. In certain embodiments, such as for small volume sample chambers, the sample chamber is sized to contain no more than about 1 µL (microliter) of sample, in some embodiments no more than about 0.5 µL, in some embodiments no more than about 0.25 µL, and in other embodiments no more than about 0.1 µL of sample, where in certain embodiments the sample chamber has a volume of no more than about 0.05 µL or even about 0.03 µL or less. A measurement zone is present within the sample chamber. The measurement zone may have the same volume, or less volume, than the sample chamber.

Embodiments of the present invention are used for the detection and quantification of an analyte, for example glucose, where in many embodiments the detection and quantification is accomplished with a small volume, e.g., submicroliter sample. In general, the invention is a sensor for analysis of an analyte in an amount, e.g., small volume, of sample by, for example, coulometry, amperometry, potentiometry or any combination thereof.

Sensors of the present invention, in some embodiments, may include two substrates forming the overall sensor construction, a spacer between the substrates, at least one working electrode, at least one counter electrode, and two or more indicator electrodes. In some embodiments, the two or more indicator electrodes may be multipurpose, functioning both as indicator electrodes and, for example, working electrodes. Together, the two substrates and spacer define a sample chamber between the substrates. At least a portion of the working electrode, counter electrode, and indicator electrodes are present in the sample chamber. The working electrode and counter electrode may be planar or facing each other.

The multiple-direction filling monitoring is particularly suited for sensors that have multiple direction filling capabilities. In some embodiments, the sensor has a sample chamber that is open or unbounded on at least two sides. An example of a sensor having at least two sides open is a sensor having a spacer between two substrates, where at least one of the substrates extends past the end of the spacer. In other words, at least one substrate cantilevers out past the spacer. In some embodiments, both substrates extend past the end of the spacer, and, for example, one substrate may extend further than the other substrate. The substrate overhang or cantilever is, in most embodiments, on the sample receiving end, side or edge of the sensor having the inlets to the sample chamber. In some embodiments, such as tip-filled sensor strips, the spacer cantilever is at the tip of the sensor strip.

These and various other features which characterize the invention are pointed out with particularity in the attached claims. For a better understanding of the sensors of the invention, their advantages, their use and objectives obtained by their use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views:

FIG. 3B is a top view of the sensor strip of FIG. 3A;

FIG. 4 is a top view of the sensor strip of FIGS. 1 and 2, the elements disassembled;

FIG. 9 is a top schematic view of another embodiment of an electrode configuration on a substrate for a sensor according to the invention;

DETAILED DESCRIPTION

The sensors of the present invention may be designed to measure the concentration of an analyte in any volume of biological fluid sample, but are particularly useful in the determination of analyte concentration in a small volume of sample, e.g., a sample having a volume no more than about 1 µL, for example no more than about 0.5 µL, for example no more than about 0.25 µL, and further for example no more than about 0.1 µL. In some embodiments, the volume of sample may be as low as 0.05 µL or as low as 0.03 µL or less. A biological fluid is any body fluid in which the analyte can be measured, for example, blood (which includes whole blood and its cell-free components such as plasma and serum), interstitial fluid, dermal fluid, sweat, tears, urine, and the like. In some embodiments the biological fluid is blood, and the analyte of interest is glucose or lactate.

An "electrochemical sensor", "electrochemical sensor strip", "biosensor", and variations thereof, is a device configured to detect the presence of and/or measure the concentration of the analyte. One manner of accomplishing this is via electrochemical oxidation and reduction reactions. These reactions are transduced to an electrical signal that can be correlated to an amount or concentration of analyte. As summarized above, in one embodiment of the disclosure, the sensors are sensor strips that include two substrates separated by a spacer and in many embodiments the sensor has a cantilever configuration. The surfaces of the substrates, together with the spacer, define a sample chamber.

Figure 1:
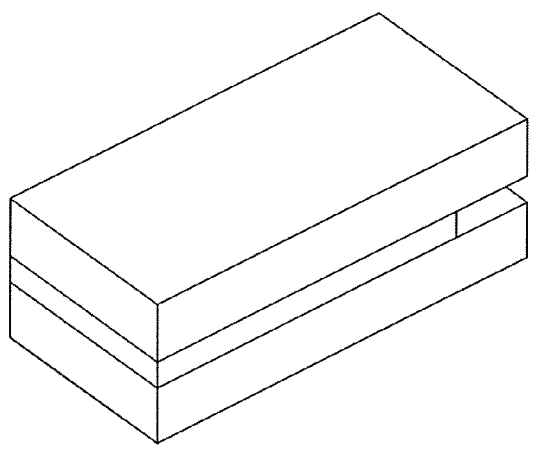
FIG. 1 is a schematic, perspective view of a first embodiment of an electrochemical sensor strip in accordance with the principles of the present invention.
Figure 2:
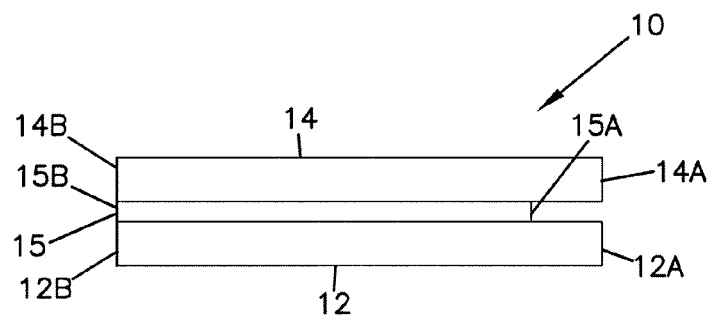
FIG. 2 is a side view of the sensor strip of FIG. 1.

Referring to the Drawings in general and FIGS. 1-3 in particular, a first embodiment of an electrochemical sensor strip 10 of the invention is schematically illustrated. The invention is described herein primarily with respect to an electrochemical sensor strip for exemplary purposes only, however, the sensor may be any suitable shape. Sensor strip 10 has a first substrate 12, a second substrate 14, and a spacer 15 positioned therebetween. Sensor strip 10 is a layered construction, in this particular embodiment, having a generally rectangular shape, i.e., its length is longer than its width, although other shapes are possible as well.

As will be described below, in some embodiments, sensor strip 10 includes at least one working electrode, at least one counter electrode (e.g., two counter electrodes), and at least two indicator electrodes (e.g., two indicator electrodes). In other embodiments, sensor strip 10 includes at least two working electrodes (e.g., two working electrodes) and at least two indicator electrodes (e.g., two indicator electrodes); in such a configuration, the at least two indicator electrodes also function as counter electrodes. These electrodes are present in a sample chamber, which may be filled from at least two directions.

Referring to FIG. 2, first or bottom substrate 12 has a first end 12A and an opposite second end 12B. Second or top substrate 14 has a first end 14A and an opposite second end 14B. Spacer 15 has a first or front (sample filling) end 15A and an opposite second end 15B. For this disclosure, first ends 12A, 14A, 15A are considered the "distal end" and second ends 12B, 14B, 15B are considered the "proximal end". At the distal end of sensor strip 10, substrate ends 12A, 14A extend past spacer end 15A. In such a construction, each of substrates 12, 14 are cantilevered substrates, extending past spacer 15.

Substrate 12 extends past spacer 15 (that is, end 12A extends past end 15A) a length designated reference number 18. Similarly, substrate 14 extends past spacer 15 (that is, end 14A extends past end 15A) a length designated by reference number 16.

Figure 3A:
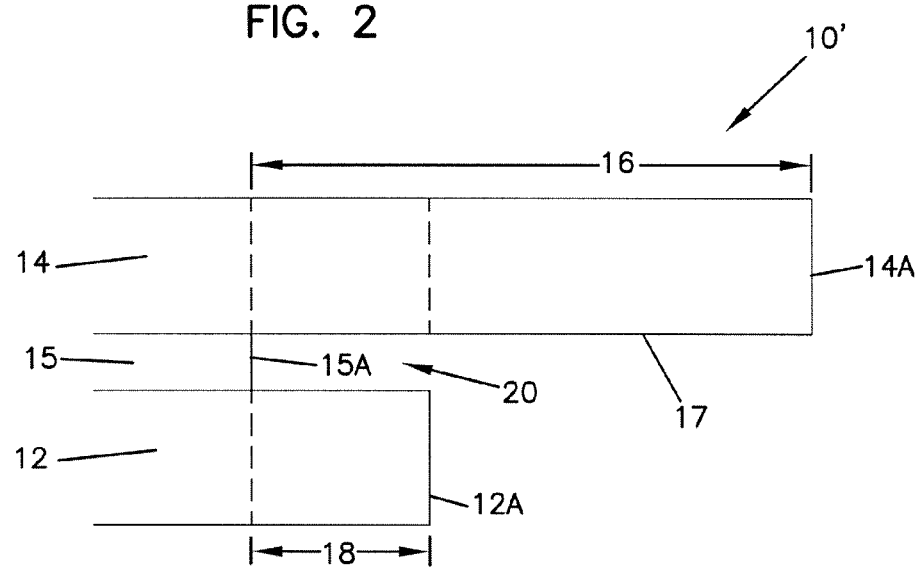
FIG. 3A is an enlarged view of a first end of an alternate sensor strip.

An alternate configuration of a cantilevered sensor, which also has an overhang, is illustrated in FIG. 3A. Similar to sensor 10 of FIGS. 1 and 2, sensor 10' has first substrate 12 with end 12A and second substrate 14 with end 14A, and positioned therebetween is spacer 15 with end 15A. Ends 12A, 14A are displaced from one another so that a portion of substrate 14 extends beyond end 12A of substrate 12 in the direction of the longitudinal axis of the sensor. This displacement of the substrate(s) relative to each other provides an overhang 17. This overhang 17 is the length of cantilever length 16 less cantilever length 18.

The dimensions of a sensor may vary. In certain embodiments, the overall length of sensor strip 10, 10' may be no less than about 20 mm and no greater than about 50 mm. For example, the length may be between about 30 and 45 mm, e.g., about 30 to 40 mm. It is understood, however, that shorter and longer sensor strips 10, 10' could be made. In certain embodiments, the overall width of sensor strip 10, 10' may be no less than about 3 mm and no greater than about 15 mm. For example, the width may be between about 4 and 10 mm, about 5 to 8 mm, or about 5 to 6 mm. In one particular example, sensor strip 10 has a length of about 32 mm and a width of about 6 mm. In another particular example, sensor strip 10, 10' has a length of about 40 mm and a width of about 5 mm. In yet another particular example, sensor strip 10, 10' has a length of about 34 mm and a width of about 4 mm.

Substrates

Substrates 12, 14 are non-conducting, inert substrates which form the overall shape and size of sensor strip 10, 10'. Substrates 12, 14 may be substantially rigid or substantially flexible. In certain embodiments, substrates 12, 14 are flexible or deformable. Examples of suitable materials for substrates 12, 14 include, but are not limited, to polyester, polyethylene, polycarbonate, polypropylene, nylon, and other "plastics" or polymers. Other non-conducting materials may also be used. One or both of substrates 12, 14 may be or include a transparent portion.

Spacer Layer

Spacer 15 is positioned between and separates first substrate 12 from second substrate 14. Spacer 15 is usually an inert non-conducting substrate, but can alternately be a semi-conductive material, such as a conducting adhesive (e.g., a one-directional conducting adhesive). Spacer 15 is typically at least as flexible and deformable (or as rigid) as substrates 12, 14. In certain embodiments, spacer 15 is an adhesive layer or double-sided adhesive tape or film. Any adhesive selected for spacer 15 should be selected to prevent or minimize diffusion or the release of material that may interfere with accurate analyte measurement.

The thickness of spacer 15 generally defines the depth or thickness of the sample chamber. In certain embodiments, the thickness of spacer 15 may be at least about 0.01 mm (10 µm) and no greater than about 1 mm or about 0.5 mm. For example, the thickness may be between about 0.02 mm (20 µm) and about 0.2 mm (200 µm). In one certain embodiment, the thickness is about 0.05 mm (50 µm), and about 0.1 mm (100 µm) in another embodiment.

For cantilevered embodiments, the length of spacer 15 may be less than the length of substrate 12 and/or of substrate 14. The width of spacer 15 may be the same or different than the widths of the substrates.

Substrate Overhang

As mentioned above, for a cantilevered sensor strip, at least one of substrates 12, 14 extends past spacer 15 at the distal end; in particular, first end 12A extends past first end 15A forming cantilever 18 and/or first end 14A extends past first end 15A forming cantilever 16. If one cantilever 16, 18 is longer than the other, overhang 17 is formed, e.g., first end 14A extends past first end 12A.

The dimensions of cantilever 16, 18 may vary. For ease of description, cantilever 16, 18 may be characterized with respect to the overall length of sensor strip 10, 10'. For example, cantilever 16 may range from about 0.05% to about 50% of the length of sensor strip 10, e.g., from about 1% to about 20% of the length of sensor strip 10, e.g., from about 4% to about 10%, e.g., about 6% of the length of sensor strip 10, 10', although larger and smaller overhangs could be used. Cantilever 16, 18 may have a length of, or in other words, second substrate 14 may extend past spacer layer 15 by at least, about 0.25 mm, e.g., at least about 0.5 mm, or e.g., at least about 1 mm. In certain embodiments, cantilever 16 may be no more than about 20 mm. A cantilever 16, 18 of about 2 mm is one specific example.

If present, the dimensions of overhang 17 may vary. One manner of characterizing overhang 17 is with respect to the overall length of sensor strip 10'. For example, overhang 17 may range from about 0.5% to about 20% of the overall length of strip 10', e.g., about 1% to about 10%, e.g., about 2% to about 5%, e.g., about 3% the length of strip 10'. In certain embodiments, overhang 17 may be at least about 0.1 mm, and in some embodiments, at least about 0.25 mm, at least about 0.5 mm, and in some other embodiments, at least about 1 mm. In certain embodiments, overhang 17 may be no more than about 10 mm, e.g., no more than about 5 mm, e.g., about 1 mm, e.g., about 0.25 mm to about 0.5 mm, whereas an overhang may be about 0.1 mm in certain embodiments.

Sample Chamber

Still referring to FIG. 3A and now to FIGS. 3B and 4, sensor strip 10, 10' includes a sample chamber 20 for receiving a volume of sample to be analyzed. Sample chamber 20 is configured so that when a sample is provided in chamber 20, the sample is in electrolytic contact with both the working electrode and the counter electrode, which allows electrical current to flow between the electrodes to effect the electrolysis (electrooxidation or electroreduction) of the analyte either directly at an electrode or via one or more electron transfer agents (e.g., redox mediators and/or enzymes).

In the embodiment of FIGS. 3A, 3B and 4, sensor strip 10, 10' is configured to receive a sample into sample chamber 20 at the distal end of sensor strip 10, 10'; this distal end is the sample receiving end of sensor strip 10, 10'.

As noted above, sample chamber 20 is defined, in part, by substrate 12, substrate 14 and by end 15A of spacer 15. Cantilever 18 is the portion of substrate 12 that defines sample chamber 20 and the portion of cantilever 16 that is not part of overhang 17 (if present) also defines sample chamber 20. Accordingly, overhang 17 extends from, and is in communication with, sample chamber 20.

As shown, a portion of the sample chamber perimeter is open or unbounded; in certain embodiments, a substantial portion is unbounded, equal to or greater than a majority of the perimeter of the sample chamber. As shown in FIG. 3B, this particular sample chamber 20 may be characterized as having sides such that three elements, substrate 12, substrate 14 and first end 15A, define three sides of sample chamber 20. At least one other side of sample chamber 20 is open, and in this embodiment, three other sides of sample chamber 20 are open.

Referring to FIG. 3B, a top view of sensor strip 10' is illustrated. From this view, sample chamber 20 has sides 20A, 20B, 20C, 20D. Sides 20A, 20C and 20D are open to the atmosphere, that is, they are not bounded. Side 20A is defined as the location where first substrate 12 terminates at first end 12A. Side 20B is defined by first end 15A of the spacer. Sides 20C, 20D are aligned with the side edges of substrates 12, 14. It is understood that in other embodiments, sample chambers may be designed that have, e.g., more sides, less sides, curved sides, or otherwise differ from sample chamber 20.

Samples chambers are filled through an open side. Sample chambers such as sample chamber 20, having more than one side unbounded or open to the atmosphere, have more than one possible inlet for sample into the sample chamber. For sample chamber 20, there are three possible inlets or inlet regions, via side 20A, side 20C and side 20D. Sample chamber 20 has multiple fill directions. In this particular embodiment, sample chamber 20 may be filled via any of sides 20A, 20C or 20D, along the entire length of any of those sides, or only at one end of any of those sides. Corner filling may also be used, for example, filling at the intersection of sides 20A and 20C, or sides 20A and 20D. Additional examples of corner-fill sensors are provided in Applicant's pending application Ser. No. 11/282,001, filed Nov. 17, 2005.

Sample chamber 20 has a volume sufficient to receive a sample of biological fluid therein. In some embodiments, such as when sensor strip 10 is a small volume sensor, sample chamber 20 has a volume that is no more than about 1 µL, for example no more than about 0.5 µL, and also for example, no more than about 0.25 µL. A volume of no more than about 0.1 µL is also suitable for sample chamber 20, as are volumes of no more than about 0.05 µL and no more than about 0.03 µL. Sample chamber 20 may have a volume greater than about 1 µL.

A measurement zone is contained within sample chamber 20 and is the region of the sample chamber that contains only that portion of the sample that is interrogated during the analyte assay. In some embodiments, the measurement zone has a volume that is no more than about 1 µL, for example no more than about 0.5 µL, also for example, no more than about 0.25 µL or even no more than about 0.1 µL. Volumes of no more than about 0.05 µL and no more than about 0.03 µL are also suitable volumes for a measurement zone. For these measurement zone volumes provided, the volume of sample chamber 20 may be no more than, for example, about 1 µL, or may be greater than about 1 µL. In some embodiments, the measurement zone has a volume that is approximately equal to the volume of sample chamber 20. In some embodiments the measurement zone includes 100% of the sample chamber or less, e.g., 80% or less, e.g., 75% or less.

Electrodes

To perform an assay, sensor strip 10 includes a plurality of electrodes, working electrode(s) and counter/reference electrode(s). In accordance with the present invention, sensor strip 10 includes at least two arrangements of electrodes on one of substrates 12, 14, to detect when sample chamber 20 has been sufficiently filled, to detect partial filling of the sample chamber and/or measurement zone. The first electrode arrangement is a pair of electrodes. The second electrode arrangement can be a single electrode or a pair of electrodes. Under some conditions, e.g., when cantilever 18 is very small and the chance of partial fill in the longitudinal direction is small, a single electrode can function as the second electrode arrangement. The following general description of various electrodes is directed to the configuration illustrated in FIG. 4. It should be understood that other electrode configurations are possible and that fall within the scope of this invention.

Working Electrode

Sensors include at least one working electrode, e.g., positioned on first substrate 12 or second substrate 14. A working electrode is an electrode at which analyte is electrooxidized or electroreduced with or without the agency of a redox mediator. Referring to FIG. 4, in this embodiment, working electrode 22 is present on second substrate 14. Working electrode 22 includes a conductive trace 26 extending to the proximal end of substrate 14, such as for connecting to a meter.

Examples of suitable materials for working electrode 22 include conductive materials such as gold, carbon, platinum, ruthenium dioxide, palladium, or other non-corroding, conducting material. The material of working electrode 22 typically has relatively low electrical resistance and is typically electrochemically inert over the potential range of the sensor during operation. An example of a suitable conductive epoxy is ECCOCOAT CT5079-3 Carbon-Filled Conductive Epoxy Coating (available from W.R. Grace Company, Woburn, Mass.).

Working electrode 22 may be applied to substrate 14 by any of various methods. Electrode 22 may be deposited, such as by vapor deposition or vacuum deposition, sputtered, printed on a flat surface or in an embossed or otherwise recessed surface, transferred from a separate carrier or liner, etched, or molded. Screen-printing is a suitable method for applying working electrode 22, although other methods such as piezoelectric printing, ink jet printing, laser printing, photolithography, and painting may be used.

Working electrode 22 is provided in sample chamber 20 for the analysis of analyte, in conjunction with the counter electrode, as will be described below.

Counter Electrode

Sensor strip 10 typically includes at least one counter electrode positioned within sample chamber 20 on either substrate 12, 14. A counter electrode is an electrode, used in conjunction with a working electrode, through which passes an electrochemical current equal in magnitude and opposite in sign to the current passed through the working electrode. Referring to FIG. 4, two counter electrodes 24 are illustrated on substrate 12. Each counter electrode 24 includes a conductive trace 28 extending to the proximal end, such as for connecting to a meter.

Counter electrode 24 may be constructed in a manner similar to working electrode 22. Counter electrode 24 may also be a counter/reference electrode. Alternatively, a separate reference electrode may be provided in contact with the sample chamber. Suitable materials for the counter electrode, counter/reference or reference electrode include Ag/AgCl or Ag/AgBr applied (e.g., printed) on a non-conducting base material or silver chloride on a silver metal base. The same materials and methods may be used to make counter electrode 24 as are available for constructing working electrode 22, although different materials and methods may also be used. Counter electrode 24 may include a mix of multiple conducting materials, such as Ag/AgCl and carbon.

Indicator Electrodes

In some embodiments, sensor strip 10 includes at least two indicator electrodes positioned on first substrate 12 and/or second substrate 14; in FIG. 4, two indicators electrodes 25 are illustrated on substrate 12. Each indicator electrode 25 includes a conductive trace 29 extending to the proximal end, such as for connecting to a meter.

Indicator electrodes 25 detect when sample chamber 20 has been sufficiently filled with sample, to prevent obtaining a measurement from a partially filled sample chamber or measurement zone. Indicator electrodes 25 are positioned in sample chamber 20 in a manner so that if biological fluid sample contacts and preferably covers both indicator electrodes 25, there might be sufficient sample present to provide an accurate analyte analysis. Having indicator electrodes 25 detect sufficient sample is the first step for determining whether sufficient sample is indeed present. Additionally discussion is provided below.

As discussed above, sample chamber 20, having three sides 20A, 20C, 20D unbounded or open to the atmosphere, has at least three possible inlets for sample into the sample chamber. In accordance with the present invention, indicator electrodes 25, together with another electrode arrangement, are appropriately positioned to monitor filling from all of the possible inlets.

Indicator electrodes 25 may be constructed in a manner similar to working electrode 22 and/or counter electrode 24. Suitable materials and methods for indicator electrodes 25 include the same materials and methods as used for working electrode 22 and/or counter electrode 24, although different materials and methods may also be used.

Electrode Configurations

Sensors of the present invention include two electrode arrangements on substrates 12, 14, to monitor sufficient filling of sample chamber 20. One electrode arrangement, e.g., a pair of indicator electrodes 25, monitors whether or not contact of the sample to the electrodes has occurred, and the second electrode arrangement determines whether or not there is sufficient sample to perform the assay. When the second electrode arrangement is an electrode pair, there is sufficient sample when both electrodes have the same amount (e.g., percentage) of sample contact. Measurements from the second electrode pair are compared to determine whether or not full coverage of the electrodes has occurred. In some embodiments, as described above, the area of the sample chamber is sufficiently small in a direction that the second electrode pair can be replaced with a single electrode. In such embodiments, a single electrode is used as the second electrode arrangement.

The first electrode arrangement (e.g., pair) monitors for the presence of sample along a first direction or dimension of the sample chamber, and the second electrode arrangement (e.g., pair or single electrode) monitors coverage of the second electrode arrangement. The second electrode arrangement is typically positioned between the electrodes of the first pair, extending in a second dimension or direction, e.g., orthogonal to the first direction or dimension. Typically, the first direction is the larger dimension of the sample chamber.

Upon determination that sufficient sample is present, i.e., the second electrode arrangement has determined the coverage is sufficient, the electrodes are the source of a signal to the attached meter. Suitable signals include, for example, voltage, current, resistance, impedance, capacitance, or any other electronically measurable signal. The signal indicates to the meter, and/or the user, that there is sufficient sample in the measurement zone to begin the assay or display the assay results. This indication may be a visual sign and/or auditory and/or vibratory signal, or the meter may be configured to automatically initiate the assay.

Figure 5:
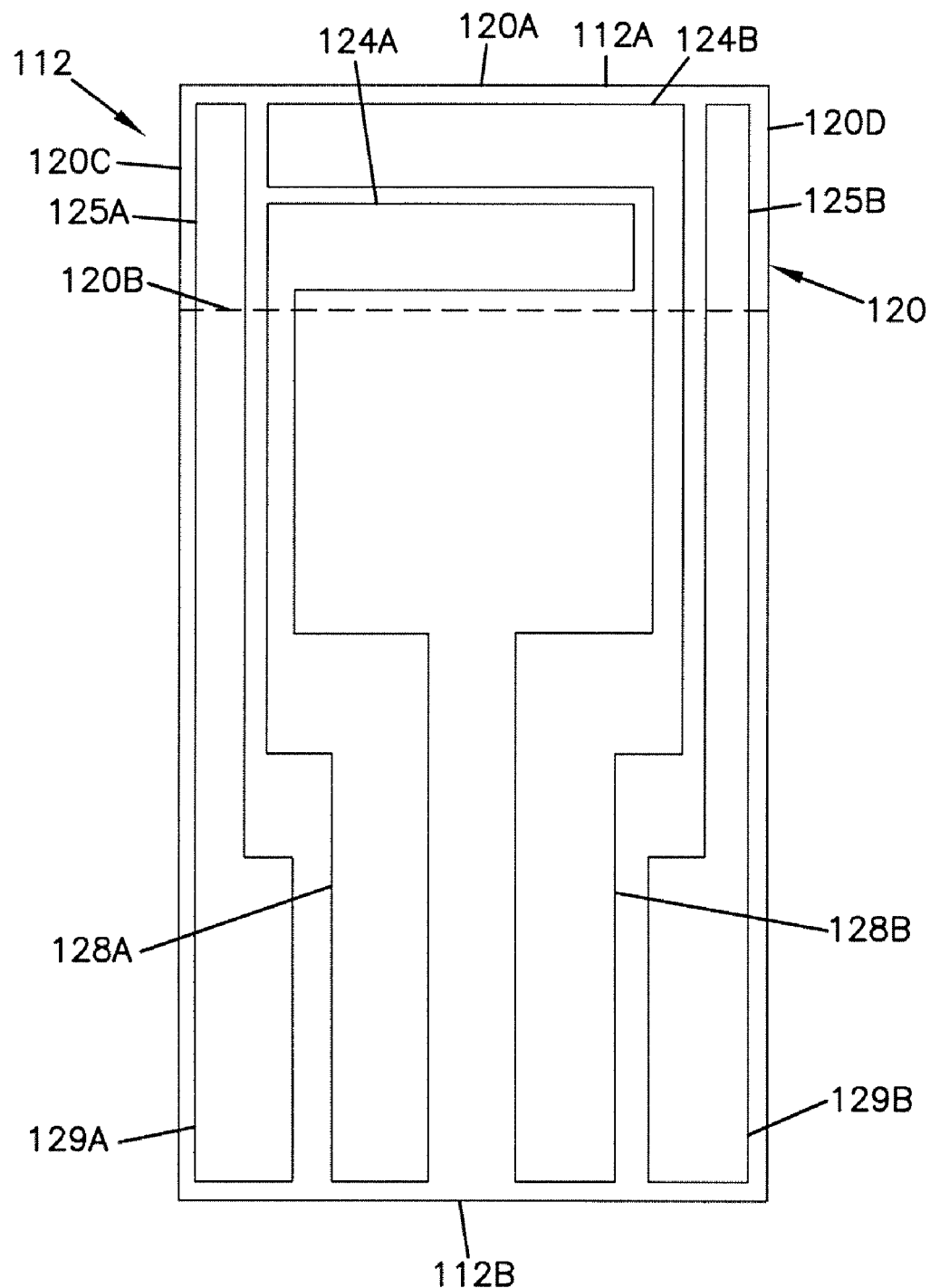
FIG. 5 is a top schematic view of an embodiment of an electrode configuration on a substrate for a sensor according to the invention.
Figure 7:
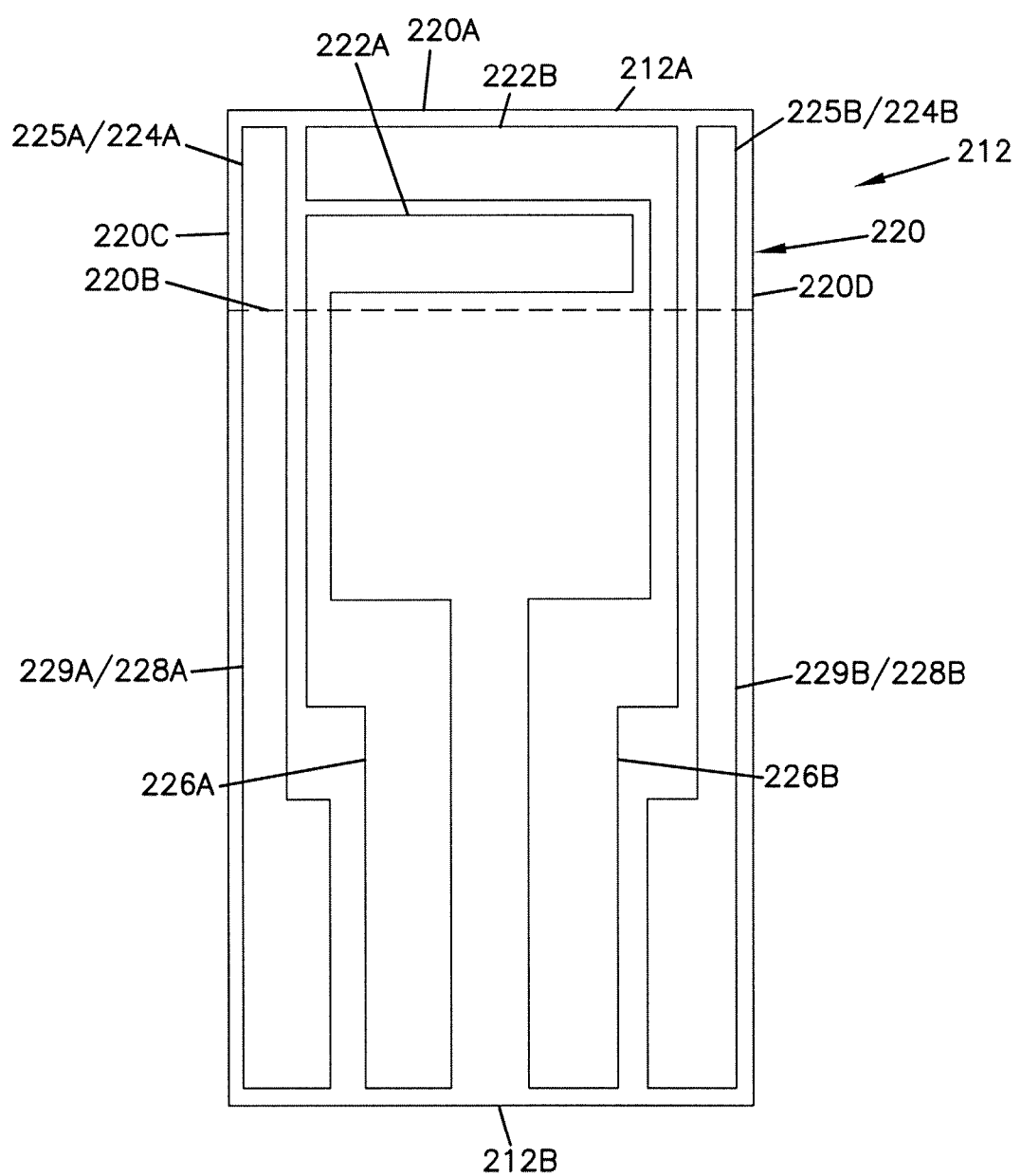
FIG. 7 is a top schematic view of another embodiment of an electrode configuration on a substrate for a sensor according to the invention.

Three specific examples of suitable electrode configurations are shown in FIGS. 5, 7 and 9. In these figures, however, only the second substrate is specifically illustrated; the first substrate is not shown. In FIG. 5, the sensor having this electrode configuration has the working electrode and counter electrodes disposed on opposite substrates facing each other to form facing electrodes. "Facing electrodes" have the working surface of the working electrode in approximate opposition to a surface of the counter electrode. In FIG. 7, the sensor having this configuration has the working electrode and counter electrode on the same substrate, to form planar or co-planar electrodes. "Planar electrodes" or "co-planar electrodes" have the working surface of a working electrode at least approximately planar to a surface of the counter electrode. "Planar electrodes" or "co-planar electrodes" are typically located on the same substrate. Both configurations include indicator electrodes.

FIG. 5, specifically, shows second substrate 112 with a counter electrode pair 124A, 124B and their respective traces 128A, 128B extending toward proximal end 112B. Also present is an indicator electrode pair 125A, 125B and their respective traces 129A, 129B. These electrodes 124A, 124B, 125A, 125B are present in the area of sample chamber 120, proximate distal end 112A of substrate 112. For this configuration, a working electrode would be present on the first substrate, which is not shown here. Sample chamber 120 has sides 120A, 120B, 120C, 120D.

Sides 120A, 120C and 120D of sample chamber 120 are unbounded. Side 120A is defined as the location where first substrate 112 terminates at first end 112A. Side 120B is defined by the first end of the spacer (not illustrated), and sides 120C, 120D are aligned with the side edges of substrate 112. The entry point for sample into sample chamber 120 could be either longitudinally into sample chamber 120 via any point along, or all of, side 120A, or laterally into sample chamber 120 via side 120C or side 120D, either any point on those sides or the entire side. Entry could also be at a corner, e.g., where side 120A and side 120C meet. The electrodes within sample chamber 120 are appropriately shaped, sized and arranged within sample chamber 120 to monitor proper filling of sample chamber 120 and contact with counter electrodes 124A, 124B, regardless of whether filling occurs via side 120A, side 120C, or side 120D.

In this embodiment, counter electrodes 124A, 124B are bounded by indicator electrodes 125A, 125B across the width of substrate 112, from side 120B to side 120D. Indicator electrodes 125A, 125B are configured to confirm filling of sample chamber 120 in the lateral direction, which is the longer dimension of sample chamber 120; that is, indicator electrodes 125A, 125B confirm that sample extends from side 120B to side 120D. Counter electrodes 124A, 124B are configured and positioned to confirm filling in the longitudinal direction of sample chamber 120, from side 120B to side 120A. Their mode of operation is discussed below.

A co-planar electrode configuration is illustrated in FIG. 7. Specifically, FIG. 7 shows second substrate 212 with working electrode pair 222A, 222B and their respective traces 226A, 226B extending toward proximal end 212B. Also present are co-function electrode pair 225A/224A, 225B/224B which electrodes function both as indicator electrodes and counter electrodes (which will be described below), and their respective traces 229A/228A, 229B/228B. These electrodes 222A, 222B, 225A/224A, 225B/224B are present in the area of sample chamber 220, proximate distal end 212A of substrate 212. Sample chamber 220 has sides 220A, 220B, 220C, 220D. Sides 220A, 220C and 220D are unbounded.

The entry point for sample into sample chamber 220 could be either longitudinally into sample chamber 220 via side 220A, or laterally into sample chamber 220 via side 220C or side 220D. Entry may be at any point of the side or the entire length of the side. Entry could also be at a corner, e.g., wherein side 220A and side 220C meet. Electrodes 225A/224A, 225B/224B are appropriately shaped, sized and arranged within sample chamber to monitor proper filling of sample chamber 220 and contact with working electrodes 222A, 222B, regardless of whether filling occurs via side 220A, side 220C, or side 220D.

In this embodiment, working electrodes 222A, 222B are bounded by electrodes 225A/224A, 225B/224B across the width of sample chamber 220, from side 220B to side 220D. Indicator electrodes 225A, 225B are configured to confirm filling in the lateral direction of sample chamber 20. Additionally, working electrodes 222A, 22B are configured and positioned to confirm filling in the longitudinal direction of sample chamber 220. After appropriate filling is confirmed, co-function electrodes 225A/224A, 225B/224B convert to counter electrodes 224A, 224B. Their mode of operation is discussed below.

The embodiments of FIGS. 5 and 7 have rectangular sample chambers 120, 220. FIG. 9 provides an embodiment having a non-rectangular sample chamber. FIG. 9, specifically, shows second substrate 312 with an electrode pair 324A, 324B and an indicator electrode pair 325A, 325B. These electrodes 324A, 324B, 325A, 325B are present in the area of sample chamber 320, which has a generally arcuate-triangular shape. Sample chamber 320 has side 320A and side 320B, with side 320B being an unbounded arcuate edge. The entire side 320B is a possible inlet region.

Electrodes 324A, 324B may be counter electrodes; a working electrode would then be positioned on an opposing substrate forming a facing electrode configuration. Alternately, electrodes 324A, 324B could be working electrodes; in this configuration, indicator electrodes 325A, 325B would be co-function electrodes, with at least one of the indicator electrodes 325A, 325B converting to a counter electrode for analyte analysis.

The entry point for sample into sample chamber 320 could be any location on side 320B. The electrodes within sample chamber 320 are appropriately shaped, sized and arranged within sample chamber 320 to monitor proper filling of sample chamber 320 and contact with electrodes 324A, 324B, and electrodes 325A, 325B, regardless of where on side 320B filling occurs.

In this embodiment, electrodes 324A, 324B are bounded by indicator electrodes 325A, 325B across the width of sample chamber 320 along side 320A. Indicator electrodes 325A, 325B are configured to confirm filling of sample chamber 320 in the lateral direction, along side 320A; indicator electrodes 325A, 325B confirm that sample extends the lengthy of side 320A. Counter electrodes 324A, 324B are configured and positioned to confirm filling in the longitudinal direction of sample chamber 320, from side 320A to the tip at side 320B.

Alternate Electrode Configuration

In other embodiments, sensors of the present invention include two electrode arrangements, one on each of substrates 12, 14, which together monitor sufficient filling of sample chamber 20. In these configurations, both electrode arrangements (e.g., pairs) work together to determine whether or not contact of the sample to the electrodes has occurred, and to determine whether or not there is sufficient sample to properly perform the assay.

Figure 10A:
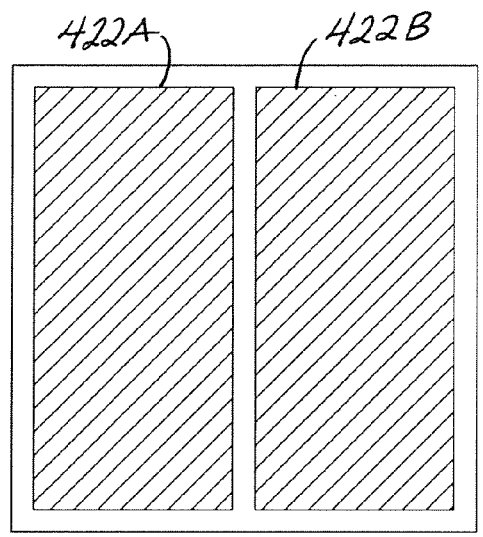
FIG. 10A is a top schematic view of yet another embodiment of an electrode configuration for a sensor according to the invention, for use with the electrode configuration of FIG. 10B.
Figure 10B:
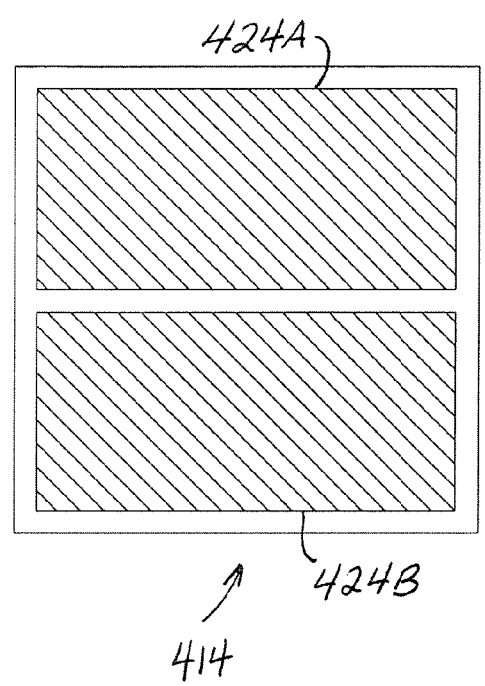
FIG. 10B is a top schematic view of an electrode configuration for a sensor for use with the electrode configuration of FIG. 10A.
Figure 10C:
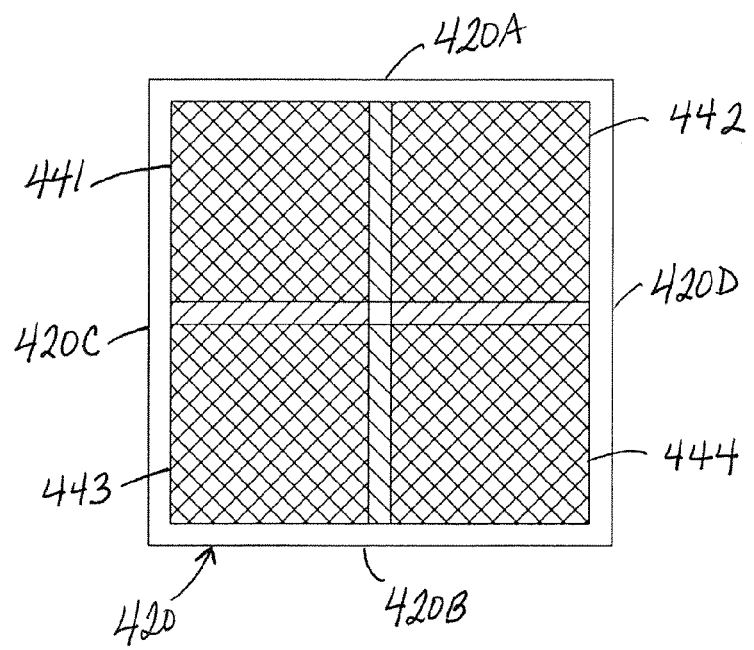
FIG. 10C is a top schematic view illustrating the two electrode configurations of FIGS. 10A and 10B combined.

In FIGS. 10A, 10B and 10C, an electrode configuration having two electrode arrangements in facing relationship is illustrated, where the first arrangement is a pair of working electrodes and the second arrangement is a pair of counter electrodes.

Referring to FIG. 10A, a first substrate 412 having thereon working electrodes 422A and 422B is illustrated, and in FIG. 10B a second substrate 414 having thereon counter electrode 424A and 424B is illustrated. The portion of substrate 412 and substrate 414 illustrated is that portion that generally defines the sample chamber of the resulting sensor. In some embodiments, the first electrode arrangement, e.g., working electrodes 422A, 422B, are positioned generally orthogonal to the second electrode arrangement, e.g., counter electrodes 424A, 424B. It is understood that each of electrodes 422A, 422B, 424A, 424B would have traces extending out from the sample chamber area to connect to, for example, a meter.

In FIG. 10C, substrates 412 and 414 are positioned in overlying orientation, as they would be when a multi-layered sensor strip is made. Typically, a spacer layer would be positioned between substrate 412 and substrate 414, which together would form a sample chamber, such as sample chamber 420.

As seen in FIG. 10C, a portion of working electrode 422A overlies a portion of each of counter electrode 424A and 424B, and similarly, a portion of working electrode 422B overlies a portion of each of counter electrode 424A and 424B. It is understood that the opposite may be done, i.e., that a portion of counter electrodes 424A, 424B overlies a portion of working electrodes 422A, 422B. These regions of overlap are illustrated as overlap 441 (i.e., overlap of working electrode 422A and counter electrode 424A), overlap 442 (i.e., overlap of working electrode 422B and counter electrode 424A), overlap 443 (i.e., overlap of working electrode 422A and counter electrode 424B), and overlap 444 (i.e., overlap of working electrode 422B and counter electrode 424B). Overlap regions 441, 442, 443, 444 are present in sample chamber 420. Sample chamber 420 is configured for fill via any of sides 420A, 420C, 420D or at corners formed by sides 420A and 420C, or sides 420A and 420D.

The electrode configuration of FIG. 10C is configured to monitor sample fill in both directions of sample chamber 420, i.e., longitudinally between sides 420A and 402B and laterally between sides 420C and 420D, based on overlap regions 441, 442, 443, 444. When sample chamber 420 is properly filled, the signal (e.g., current, voltage, etc.) received from the two electrodes of the electrode arrangements is the same, with allowable leeway for measurement errors.

For example, the signal of working electrode 422A would be the signal of overlap 441 plus the signal of overlap 443. Similarly, the signal of working electrode 422B would be the signal of overlap 442 plus the signal of overlap 444. Additionally, the signal of counter electrode 424A would be the signal of overlap 441 plus the signal of overlap 442, and the signal of counter electrode 424B would be the signal of overlap 443 plus the signal of overlap 444. In some embodiments, when sample chamber 420 is properly filled, the signal of working electrode 422A is equal to the signal of working electrode 422B, and, the signal of counter electrode 424A is equal to the signal of counter electrode 424B. If the signal of working electrode 422A is not equal to the signal of working electrode 422B, then there is not sufficient fill laterally in sample chamber 420. If the signal of counter electrode 424A is not equal to the signal of counter electrode 424B, then there is not sufficient fill longitudinally in sample chamber 420. With such an electrode arrangement as illustrated in FIGS. 10A, 10B, 10C, no separate indicator electrodes are present; the two electrode arrangements are configured and arrangement to monitor sample fill in both directions of sample chamber 420, longitudinally between sides 420A and 402B, and laterally between sides 420C and 420D.

In this example embodiment, the size or surface area of each electrode in each of the electrode arrangements is generally the same. It is understood that in other embodiments, the size of electrodes, from one arrangement to the other, or from one electrode to another, may be different. In such embodiments, the signal from the electrode, when the sample chamber is fully filled, will be directly proportional to the electrode size.

Again, as discussed above, in some embodiments, if the dimension of the sample chamber is sufficiently small in a direction, the second electrode arrangement may be replaced with a single electrode, rather than being an electrode pair. For example, referring to FIG. 10C, if the longitudinal dimension (i.e., from side 420A to side 420B) was, e.g., 10 times less than the lateral direction (i.e., from side 420C to side 420D), only one counter electrode may be present.

Sensing Chemistry

To facilitate the analysis of the analyte, sensing chemistry is provided in sample chamber 20. Sensing chemistry material facilitates the transfer of electrons between working electrode 22 and the analyte in the sample. Any suitable sensing chemistry may be used in sensor strip 10; the sensing chemistry may include one or more materials.

The sensing chemistry may be diffusible or leachable, or non-diffusible or non-leachable. A "non-diffusible," "non-leachable," or "non-releasable" compound is a compound which does not substantially diffuse away from the working surface of the working electrode for the duration of the analyte assay. For purposes of discussion herein, the term "diffusible" will be used to represent "diffusible or leachable" and the term "non-diffusible" will be used to represent "non-diffusible or non-leachable" and variations thereof. Placement of sensing chemistry components may depend at least in part on whether they are diffusible or not. For example, both non-diffusible and/or diffusible component(s) may form a sensing layer on working electrode 22. Alternatively, one or more diffusible components may be present on any surface in sample chamber 20 prior to the introduction of the sample to be analyzed. As another example, one or more diffusible component(s) may be placed in the sample prior to introduction of the sample into sample chamber 20.

Electron Transfer Agent

The sensing chemistry generally includes an electron transfer agent that facilitates the transfer of electrons to or from the analyte. An "electron transfer agent" is a molecule that carries electrons between either a redox mediator and the analyte or the working electrode and the analyte. The electron transfer agent may be diffusible or non-diffusible, and may be present on working electrode 22 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes may be used for other analytes.

The electron transfer agent, whether it is diffusible or not, facilitates a current between working electrode 22 and the analyte and enables the electrochemical analysis of molecules. The agent facilitates the transfer electrons between the electrode and the analyte. An electron transfer agent may be used in combination with a redox mediator.

Redox Mediator

The sensing chemistry may, additionally to or alternatively to the electron transfer agent, include a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator may be a polymeric redox mediator, or, a redox polymer (i.e., a polymer having one or more redox species). Examples of suitable redox mediators and redox polymer are disclosed in U.S. Pat. No. 6,338,790, for example, and in U.S. Pat. Nos. 6,605,200 and 6,605,201.

If the redox mediator is non-diffusible, then the redox mediator may be disposed on working electrode 22 as a layer. In an embodiment having a redox mediator and an electron transfer agent, if the redox mediator and electron transfer agent are both non-leachable, then both components are disposed on working electrode 22 as individual layers, or combined and applied as a single layer.

The redox mediator, whether it is diffusible or not, mediates a current between working electrode 22 and the analyte and enables the electrochemical analysis of molecules which may not be suited for direct electrochemical reaction on an electrode. The mediator functions as an agent to transfer electrons between the electrode and the analyte.

Operation of the Sensor

In use, a sample of biological fluid is provided into the sample chamber of the sensor, where the level of analyte is determined. In many embodiments, it is the level of glucose in blood, interstitial fluid, and the like, that is determined. Also in many embodiments, the source of the biological fluid is a drop of blood drawn from a patient, e.g., after piercing the patient's skin with a lancing device or the like, which may be present in an integrated device, together with the sensor strip.

Embodiments of the subject methods include contacting the sensor with a fluid sample (obtained, e.g., from a skin incision) and transferring a volume of the fluid to the sample chamber and measurement zone of the sensor. Accordingly, bodily fluid may be first contacted with a portion of one of the substrates of the sensor (e.g., the cantilever of a top substrate) prior to being contacted with the other substrate and/or sample chamber.

As discussed above, methods include monitoring the sample fill of the sensor, regardless of the direction of fill of the sample chamber, e.g., a lateral or longitudinal direction of fill.

One embodiment of an electrode configuration for use in monitoring sample fill of a sensor from any direction into a sample chamber is described above in reference to FIG. 5. The arrangement of a pair of indicator electrodes 125A, 125B outside of a pair of counter electrodes 124A, 124B confirm the presence of fluid in the lateral direction of sample chamber 120, across the width of substrate 112, from side 120B to side 120D. Counter electrodes 124A, 124B confirm filling in the longitudinal direction of sample chamber 120.

One suitable method embodiment for using the electrode configuration of the embodiment of FIG. 5 or analogous embodiments may be as follows:

1. prior to inputting a fluid sample, applying a voltage between indicator electrodes 125A, 125B and monitor the current therebetween; disconnecting any counter electrodes and/or working electrodes if present;

2. inputting a fluid sample into sample chamber 120 via any of sides 120A, 120C, 120D, or corners formed thereby, so that current is detected between indicator electrodes 125A, 125B, indicating that sample is present across sample chamber 120, thus triggering the analyte measurement;

3. activating the working electrode (on the first substrate) and counter electrodes 124A, 124B, and compare the signal between the working electrode and electrode 124A and the working electrode and electrode 124B; and 4. accepting or disregarding the results. For example, if the signal differential between the working electrode and electrode 124A and the working electrode and electrode 124B is within acceptable limits, the result is acceptable. If the signal differential is too large, an error is reported. The signal differential may be based on a relation, such as a ratio, of the area of electrode 124A versus electrode 124B. For example, if the area of electrode 124A to electrode 124B is 1:1, the resulting signals may be approximately 1:1, with allowable leeway for measurement errors. The signal differential may be based on other relations, such as non-linear relations.

Figure 6A:
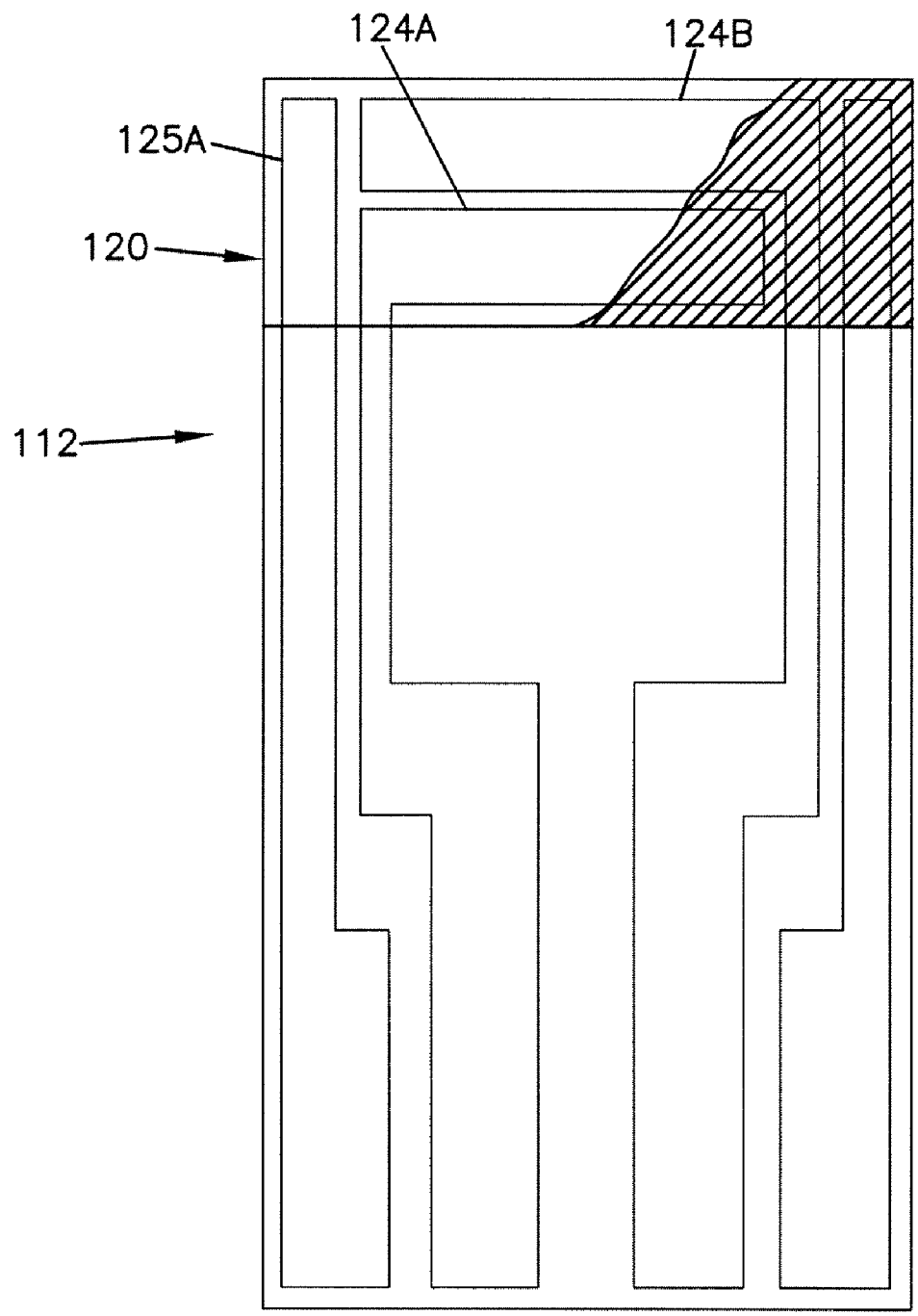
FIG. 6A is a top schematic view of the electrode configuration of FIG. 5 with the sample chamber partially filled.
Figure 6B:
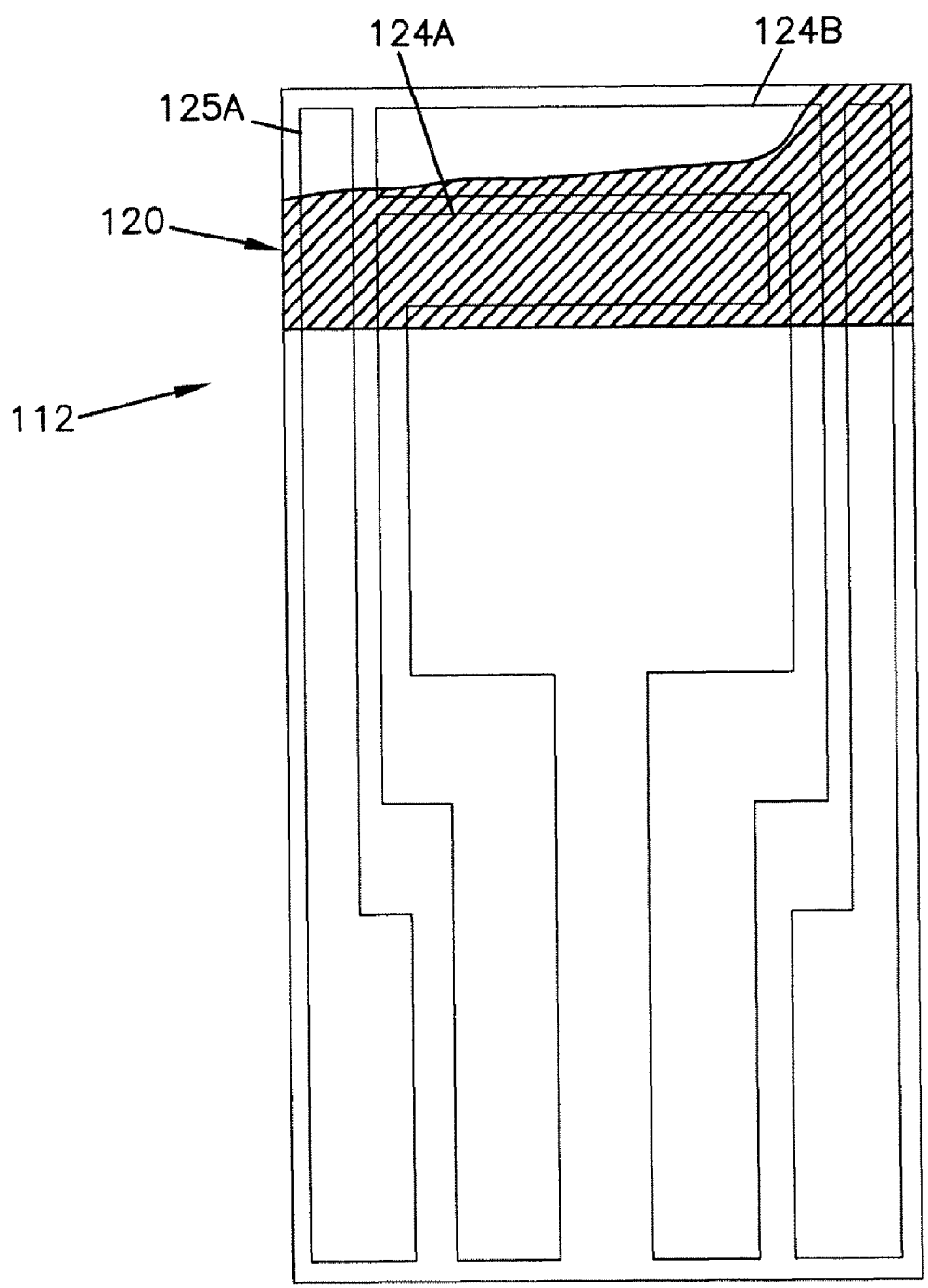
FIG. 6B is a top schematic view of the electrode configuration of FIG. 5 with the sample chamber partially filled to a different level than that of FIG. 6A.
Figure 6C:
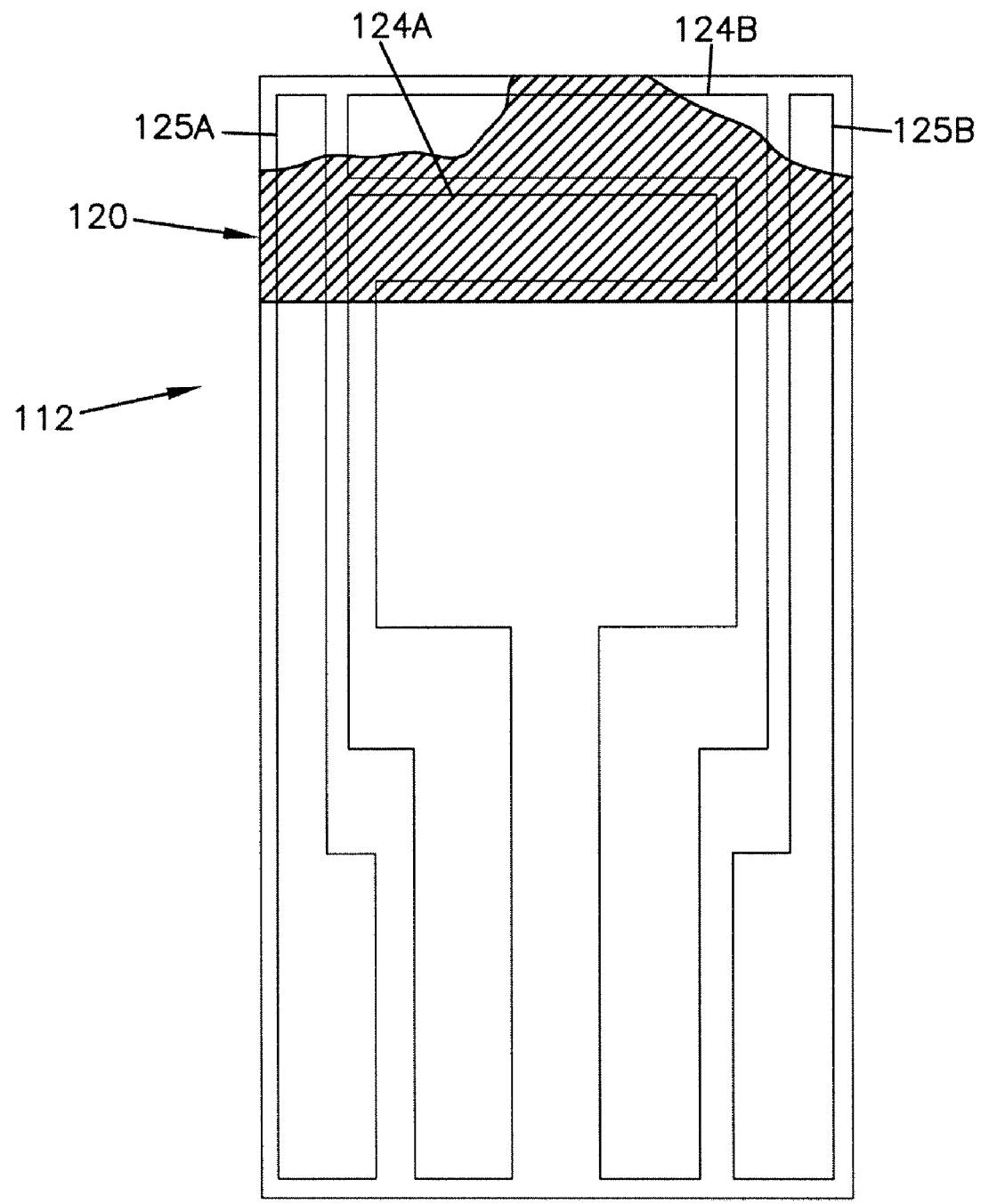
FIG. 6C is a top schematic view of the electrode configuration of FIG. 5 with the sample chamber partially filled to a different level than that of FIGS. 6A and 6B.

FIGS. 6A, 6B and 6C illustrate three unacceptable fills. In FIG. 6A, the pair of indicator electrodes 125A, 125B do not indicate sufficient amount of sample in the lateral direction. The working electrode and the counter electrode are not activated. In both FIGS. 6B and 6C, indicator electrodes 125A, 125B indicate sufficient sample in the lateral direction, and the working electrode and counter electrodes 124A, 124B activated. However, a measurement from the working electrode and counter electrode 124A is greater than that from the working electrode and counter electrode 124B, due to a greater percentage of area of counter electrode 124A being covered than of counter electrode 124B. If this difference between the two measurements is outside the acceptable limit, the results are rejected.

Another suitable method embodiment for using the electrode configuration of the embodiment of FIG. 5 or analogous embodiments may be as follows:

1. prior to inputting a fluid sample, applying a voltage between indicator electrodes 125A, 125B and monitor the current therebetween; disconnecting any voltage between counter electrodes and/or working electrodes, if present;

2. inputting a fluid sample into sample chamber 120 via any of sides 120A, 120C, 120D or corners formed thereby, so that current is detected between indicator electrodes 125A, 125B, indicating that sample is present across sample chamber 120;

3. monitoring resistance, conductivity, impedance or any electrical signal that is proportional to the electrode area covered by sample between each counter electrode 124A, 124B and indicator electrodes 125A, 125B, and triggering the analyte measurement when the signals for the two electrodes are comparable; and 4. activating the working electrode (on the first substrate) and counter electrodes 124A, 124B, and perform the measurement.

Another embodiment of an electrode configuration is described above in reference to FIG. 7. The arrangement of a pair of co-function electrodes 225A/224A, 225B/224B outside of a pair of working electrodes 222A, 222B confirm the presence of fluid in the lateral direction of sample chamber 220, across the width of substrate 212, from side 220B to side 220D; during this step, the co-function electrodes 225A/224A, 225B/224B are indicator electrodes 225A, 225B. Working electrodes 222A, 222B confirm complete filling in the longitudinal direction of sample chamber 220.

One suitable method embodiment for using the electrode configuration of the embodiment of FIG. 7 or analogous embodiment may be as follows:

1. Prior to inputting a fluid sample, applying a voltage between co-function electrodes 225A/224A, 225B/224B and monitor the current therebetween; disconnecting any voltage between counter electrodes and/or working electrodes, if present;

2. inputting a fluid sample into sample chamber 220 via any of sides 220A, 220C, 220D or corner formed thereby, so that current is detected between co-function electrodes 225A/224A, 225B/224B, indicating that sample is present across sample chamber 220 and thus triggering the analyte measurement;

3. activating the working electrodes 222A, 222B; after this point, co-function electrodes 225A/224A, 225B/224B function as counter electrodes 224A, 224B; and comparing the signal between working electrode 222A and working electrode 222B.

4. If the difference of the signal from working electrode 222A and working electrode 222B is within acceptable limits, the result is acceptable. If the signal differential is too large, an error is reported.

Figure 8A:
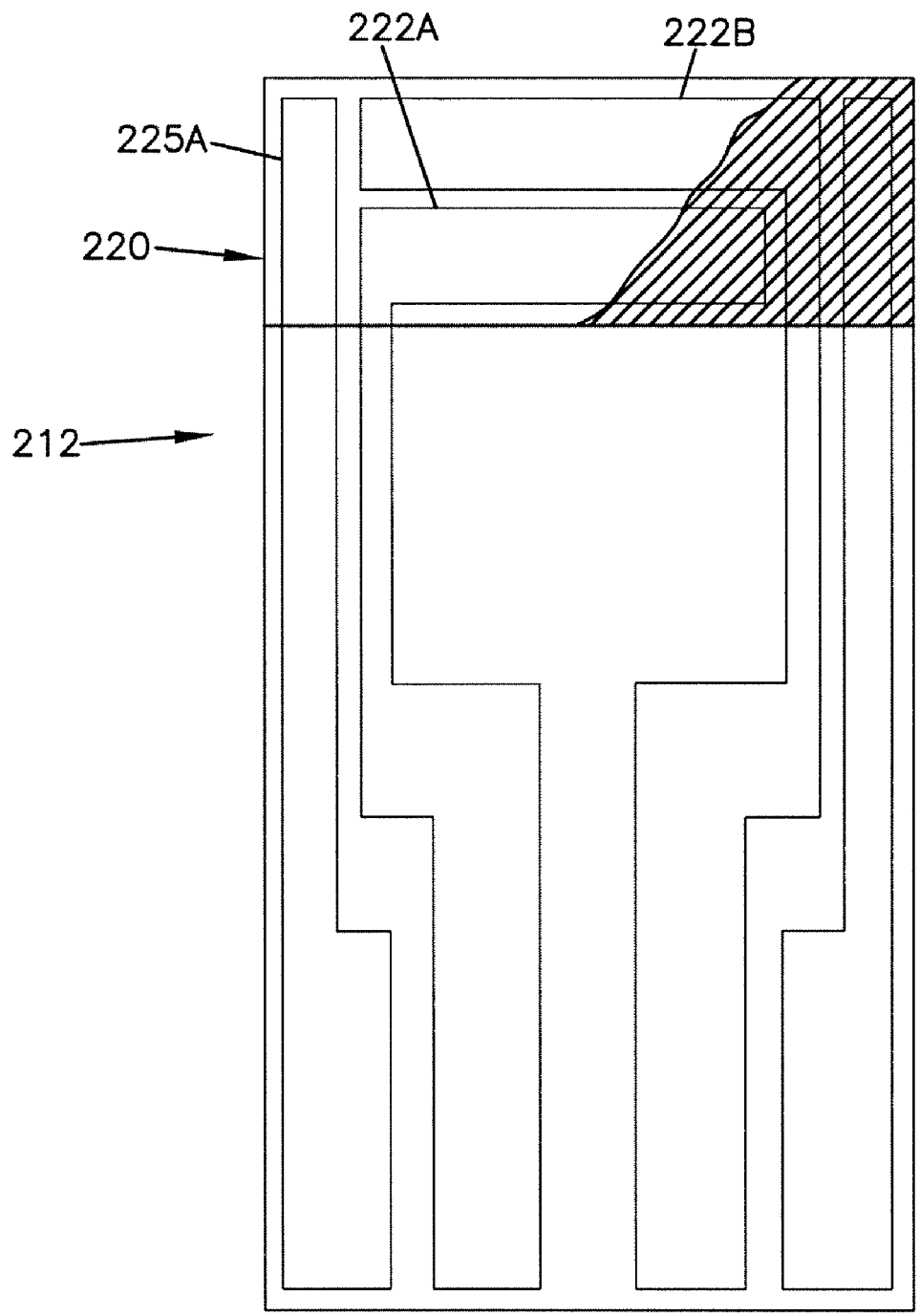
FIG. 8A is a top schematic view of the electrode configuration of FIG. 7 with the sample chamber partially filled.
Figure 8B:
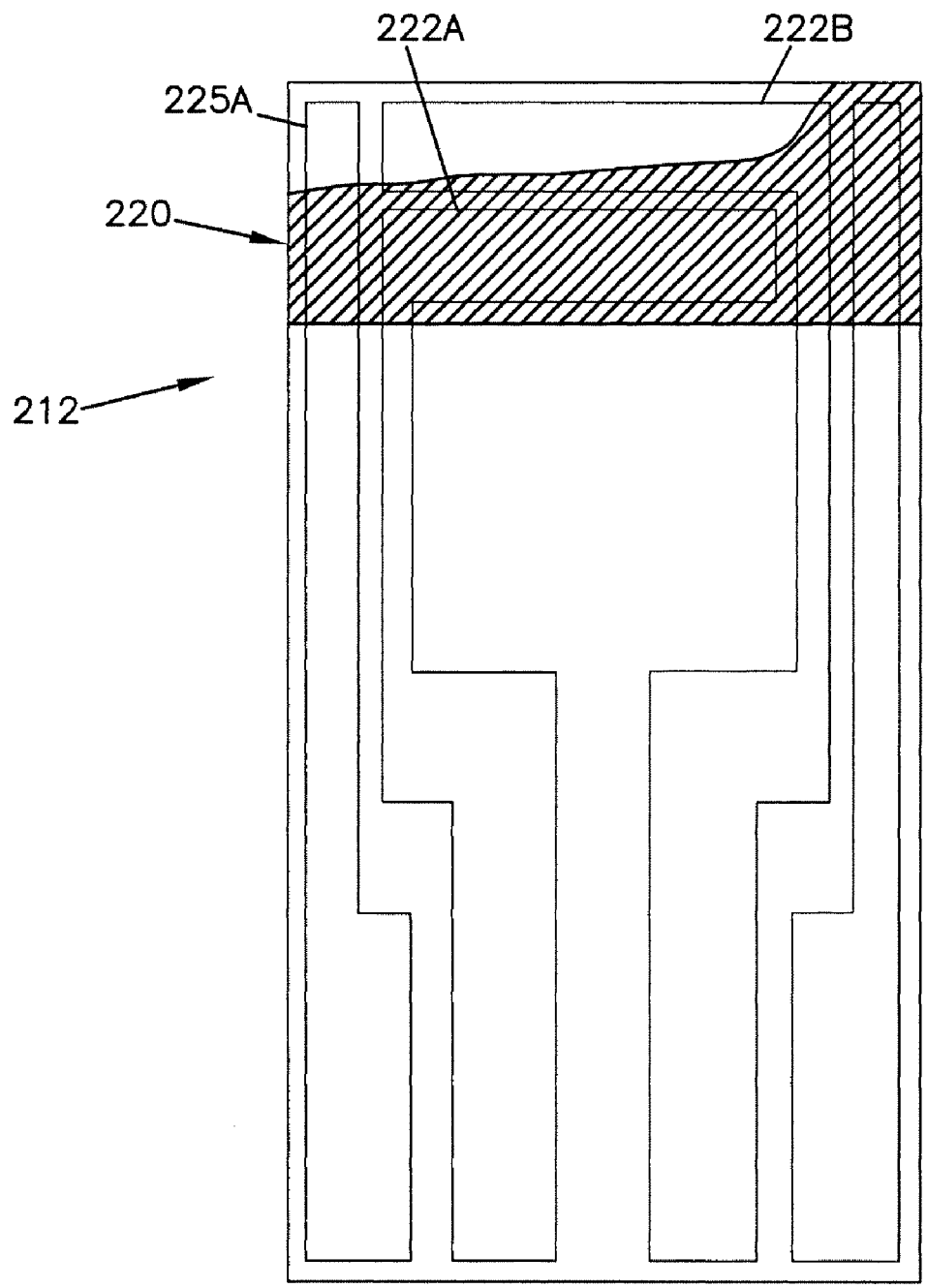
FIG. 8B is a top schematic view of the electrode configuration of FIG. 7 with the sample chamber partially filled to a different level than that of FIG. 8A.
Figure 8C:
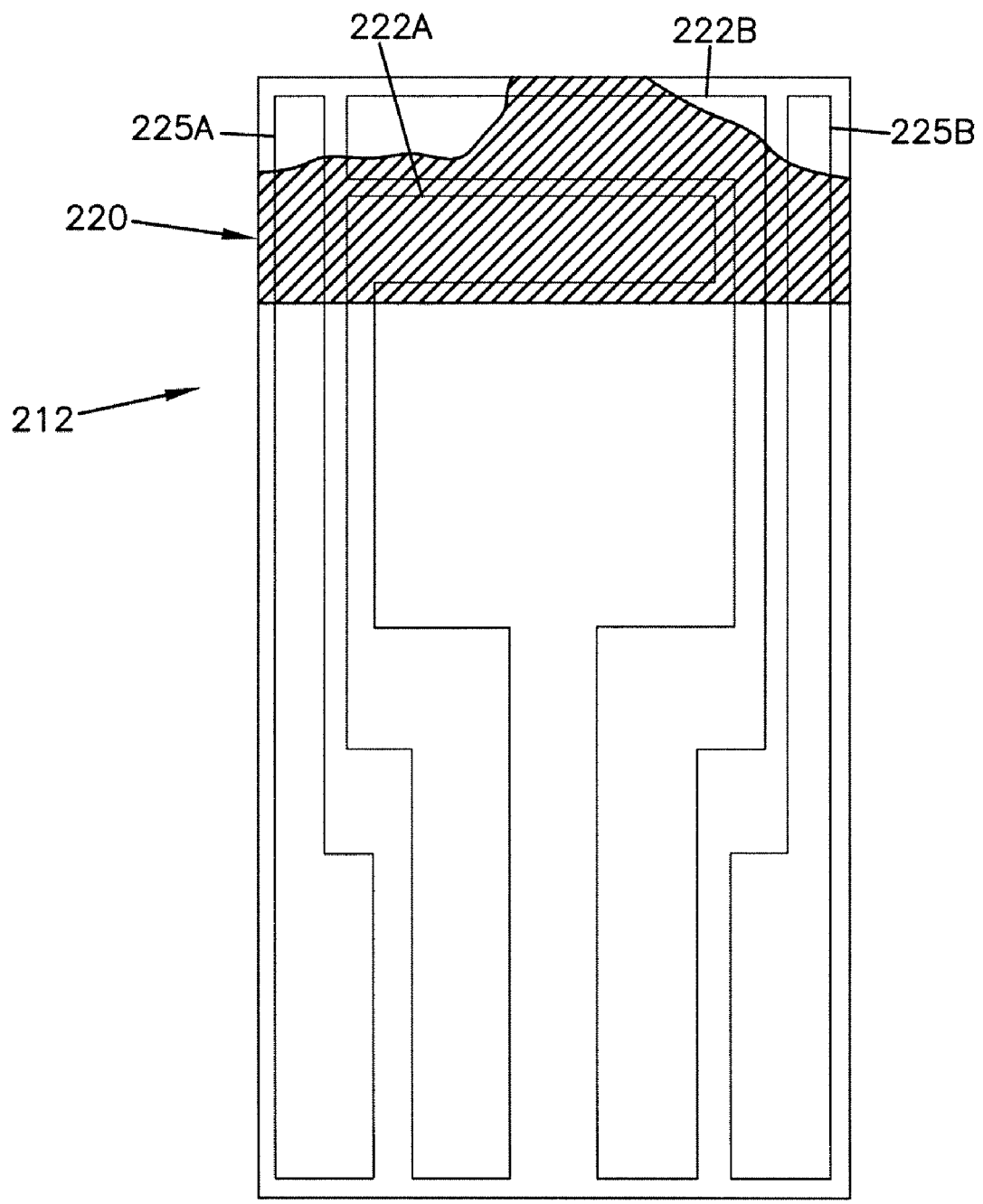
FIG. 8C is a top schematic view of the electrode configuration of FIG. 7 with the sample chamber partially filled to a different level than that of FIGS. 8A and 8B.

FIGS. 8A, 8B and 8C illustrate three unacceptable fills. In FIG. 8A, the pair of indicator electrodes 225A, 225B (specifically, co-function electrodes 225A/224A, 225B/224B) do not indicate sufficient amount of sample in the lateral direction. The working electrode pair is not triggered. In both FIGS. 8B and 8C, the pair of co-function electrodes 225A/224A, 225B/224B indicates sufficient sample in the lateral direction, and working electrodes 222A, 222B are triggered. However, a signal measurement from working electrode 222A is greater than that from working electrode 222B, due to more area of working electrode 222A being covered than of working electrode 222B. If this difference between the two signal measurements is outside the acceptable limit, the results are rejected.

Figure 8D:
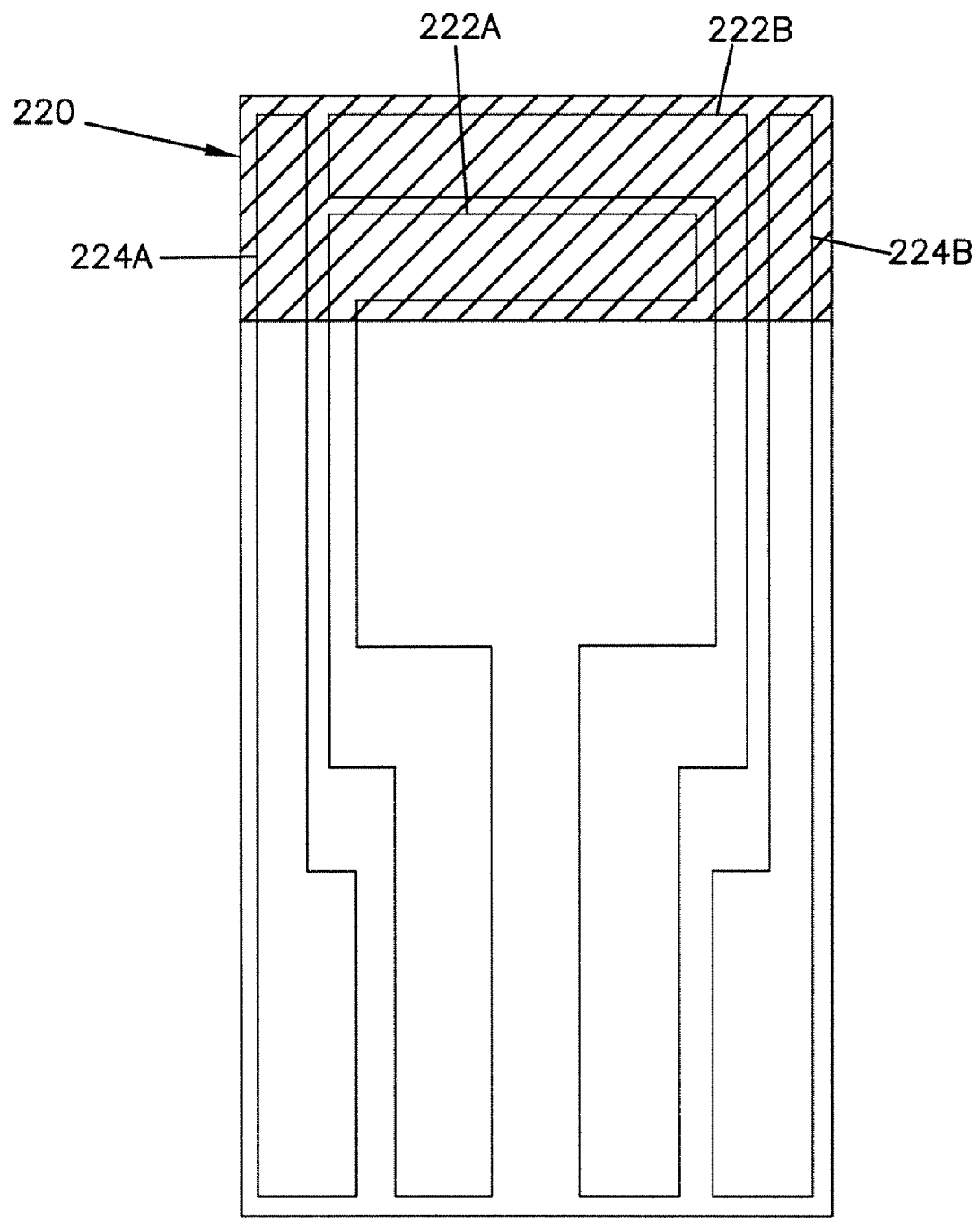
FIG. 8D is a top schematic view of the electrode configuration of FIG. 7 with the sample chamber fully filled.

FIG. 8D illustrates acceptable fill, with all electrodes covered.

Another suitable operation sequence for the electrode configuration of FIG. 7 may be as follows:

1. prior to inputting a fluid sample, applying a voltage between co-function electrodes 225A/224A, 225B/224B and monitor the current therebetween; disconnecting any voltage between working electrodes 222A, 222B, if present;

2. inputting a fluid sample into sample chamber 220 via any of sides 220A, 220C, 220D or corner formed thereby, so that current is detected between co-function electrodes 225A/224A, 225B/224B indicating that sample is present across sample chamber 220;

3. monitoring resistance, conductivity, impedance or any electrical signal that is proportional to the electrode area covered by sample for each working electrode 222A, 222B; and triggering the analyte measurement when the measurements for the two electrodes are comparable; and 4. activating the working electrodes 222A, 222B and switching co-function electrodes 225A/224A, 225B/224B to be counter electrodes 224A, 224B and performing the analyte measurement.

In some embodiments, the analysis of the analyte may not begin until the indicator electrodes indicate that sufficient sample is present to extend across the width or longitudinally dimension of the sample chamber, e.g., between two indicator electrodes, which is often the longest dimension.

In some embodiments, such as described in reference to FIGS. 10A, 10B and 10C, both electrode arrangements begin as indicator electrodes, for example, to monitor resistance, impedance, etc. When the measurements for the two electrodes are comparable indicating that the sample chamber is sufficiently full, the analyte measurement beings, and the electrode arrangements convert to working electrodes and counter electrodes.

Manufacture of the Sensors

Sensor strips 10, 10' are sandwiched or layered constructions having substrates 12, 14 spaced apart, such as by spacer 15. Such a construction may be made by laminating the various layers together, in any suitable manner. An alternate method for making sensor strips 10, 10', and other sensors in accordance with the invention, is to mold the sensors.

Molding may include positioning at least two spaced apart electrically conductive electrodes (e.g., wires) in a mold, and molding a body of insulative material around the electrodes, with one end having therein means for receiving a fluid sample. More specifically, molding could include positioning at least two spaced apart electrically conductive electrodes (e.g., wires) in a mold, before or after molding, treating at least one of the electrodes with one or more chemicals to change the electrical properties of the treated electrode upon contact with a fluid sample, and molding a body of insulative material around the electrodes with one end having therein means for receiving a fluid sample. The body may be molded in multiple pieces, e.g., two pieces, with a body and end cap for attaching to one another after the molding is completed, or in a single piece.

A sensor may be made by determining a suitable length of any cantilever or overhang for a sensor and manufacturing the sensor so that it includes such structures. For example, a sensor may be made by positioning electrodes on one or more substrates, the substrates including a first substrate having a first length and a second substrate having a second length, contacting at least a portion of at least one electrode with sensing reagent(s) and configuring the sensor by positioning a spacer between the two substrates to maintain the substrates in a fixed, layered orientation relative to each other. The substrates are positioned so that the additional length of the first sensor resides at the distal or sample receiving end of the sensor.

In some embodiments, whether the substrates are the same length or not, the substrates may be displaced relative to each other along their longitudinal axes so that one of the substrates, e.g., the top substrate, extends a distance beyond the end of the other (e.g., bottom substrate) at the sample receiving end to provide the overhang. Contact pads may be positioned at the proximal end.

Application of the Sensor

A common use for an analyte sensor of the present invention, such as sensor strip 10, is for the determination of analyte concentration in a biological fluid, such as glucose concentration in blood, interstitial fluid, and the like, in a patient or other user. Additional analytes that may be determined include but are not limited to, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Sensor strips 10 may be available at pharmacies, hospitals, clinics, from doctors, and other sources of medical devices. Multiple sensor strips 10 may be packaged together and sold as a single unit; e.g., a package of about 25, about 50, or about 100 sensors, or any other suitable number. A kit may include one or more sensors of the present invention, and additional components such as control solutions and/or lancing device and/or meter, etc.

Sensor strips 10 may be used for an electrochemical assay, or, for a photometric test. Sensor strips 10 are generally configured for use with an electrical meter, which may be connectable to various electronics. A meter may be available at generally the same locations as sensor strips 10, and sometimes may be packaged together with sensor strips 10, e.g., as a kit.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touchscreen. With such an arrangement, the user can control the meter indirectly by interacting with the user interface(s) of the server device, which in turn interacts with the meter across a wireless link.

The server device may also communicate with another device, such as for sending data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as sensor strips 10 and the meter, and sometimes may be packaged together with sensor strips 10 and/or meter, e.g., as a kit.

Sensor strips 10 are particularly suited for inclusion in an integrated device, i.e., a device which has the sensor and a second element, such as a meter or a lancing device, in the device. The integrated device may be based on providing an electrochemical assay or a photometric assay. In some embodiments, sensor strips 10 may be integrated with both a meter and a lancing device. Having multiple elements together in one device reduces the number of devices needed to obtain an analyte level and facilitates the sampling process. For example, embodiments may include a housing that includes one or more of the subject strips, a skin piercing element and a processor for determining the concentration of an analyte in a sample applied to the strip. A plurality of strips 10 may be retained in a cassette in the housing interior and, upon actuation by a user, a single strip 10 may be dispensed from the cassette so that at least a portion extends out of the housing for use.

The invention has been described with reference to various specific and preferred embodiments and techniques. However, it will be apparent to one of ordinarily skill in the art that many variations and modifications may be made while remaining within the spirit and scope of the invention.

All patents, applications and other references in this specification are indicative of the level of ordinary skill in the art to which this invention pertains. All patents, patent applications and other references are herein incorporated by reference to the same extent as if each individual patent, application or reference was specifically and individually incorporated by reference.

What is claimed:

1. A sensor for determining the concentration of an analyte in a sample, the sensor comprising:
    a sample chamber;
    a first electrode pair, wherein electrodes of the first electrode pair are spaced in a lateral direction with respect to each other in the sample chamber, and
    a second electrode pair, wherein electrodes of the second electrode pair each comprise an electrode portion and a trace portion and wherein entire electrode portions of the electrodes of the second electrode pair are spaced in a longitudinal direction with respect to each other in the sample chamber,
    wherein the second electrode pair is positioned in between the first electrode pair.

2. The sensor of claim 1, wherein the electrode portions of the electrodes of the second electrode pair are substantially rectangular.

3. The sensor of claim 1, wherein the sensor further comprises a first substrate, a second substrate, and a sample receiving end, wherein the sample chamber is positioned between the first and second substrates, wherein the sensor further comprises an overhanging substrate wall at the sample receiving end of the sensor, and wherein the sample chamber comprises at least two unbounded sides at the sample receiving end of the sensor.

4. The sensor of claim 1, wherein the first electrode pair comprises a pair of electrodes that functions as indicator electrodes and counter electrodes and the second electrode pair is a pair is a pair of working electrodes.

5. The sensor of claim 1, wherein the second electrode pair comprises a pair of electrodes that functions as indicator electrodes and counter electrodes and the first electrode pair is a pair is a pair of working electrodes.

6. The sensor of claim 1, wherein the second electrode pair comprises a pair of working electrodes.

7. The sensor of claim 1, wherein the second electrode pair comprises a pair of counter electrodes.

8. The sensor of claim 1, wherein about 10% to about 95% of perimeter of the sample chamber is unbounded.

9. The sensor of claim 8, wherein about 50% to about 95% of perimeter of the sample chamber is unbounded.

10. The sensor of claim 1, wherein the sample chamber comprises at least two unbounded sides.

11. The sensor of claim 10, wherein the sample chamber comprises three unbounded sides.

12. The sensor of claim 1, wherein the sample chamber has a volume of no more than about 1 microliter.

13. The sensor of claim 12, wherein the sample chamber has a volume of no more than about 0.5 microliter.

14. The sensor of claim 13, wherein the sample chamber has a volume of no more than about 0.1 microliter.

15. The sensor of claim 1, wherein the sensor further comprises a first substrate and a second substrate, a spacer between the first substrate and the second substrate, together the first substrate, second substrate and spacer defining at least a portion of the sample chamber, wherein the first electrode pair and the second electrode pair are placed on the first substrate.

16. The sensor of claim 15, wherein the first electrode pair comprises a pair of indicator electrodes.

17. The sensor of claim 16, wherein the second electrode pair comprises a pair of counter electrodes.

18. The sensor of claim 17, wherein the sample chamber further comprises a working electrode placed on the second substrate.

\* \* \* \* \*

UNITED STATES PATENT AND TRADEMARK OFFICE
CERTIFICATE OF CORRECTION

PATENT NO. : 7,887,682 B2
APPLICATION NO. : 11/277931
DATED : February 15, 2011
INVENTOR(S) : Yi Wang et al.

Page 1 of 1

It is certified that error appears in the above-identified patent and that said Letters Patent is hereby corrected as shown below:

Col. 18, line 29, please delete the second occurrence of "is a pair."

Col. 18, line 33, please delete the second occurrence of "is a pair."

Signed and Sealed this
Twenty-first Day of June, 2011

David J. Kappos
*Director of the United States Patent and Trademark Office*